United States Patent
Godfried et al.

(10) Patent No.: US 6,699,236 B1
(45) Date of Patent: Mar. 2, 2004

(54) CUTTING BLADE FOR SURGICAL INSTRUMENT

(76) Inventors: Herman Philip Godfried, Dulkruid 57, NL-7491 LP, Delden (NL); Paulus Gerardus Hendrickus Maria Spaaij, Watersnipstraat 32, NL-6601 EG, Wijchen (NL)

( * ) Notice: Subject to any disclaimer, the term of this patent is extended or adjusted under 35 U.S.C. 154(b) by 0 days.

(21) Appl. No.: 10/019,552
(22) PCT Filed: Jun. 29, 2000
(86) PCT No.: PCT/IB00/00876
§ 371 (c)(1), (2), (4) Date: May 21, 2002
(87) PCT Pub. No.: WO01/00100
PCT Pub. Date: Jan. 4, 2001

(30) Foreign Application Priority Data

Jun. 29, 1999 (ZA) ............................... 99/4256

(51) Int. Cl.[7] ................................ A61B 18/20
(52) U.S. Cl. ................ 606/2; 606/13; 606/17
(58) Field of Search ........................ 606/1–19

(56) References Cited

U.S. PATENT DOCUMENTS

| | | | |
|---|---|---|---|
| 4,209,017 A | | 6/1980 | Shaw ..................... 128/303.1 |
| 4,627,435 A | * | 12/1986 | Hoskin ..................... 128/303.1 |
| 5,320,620 A | * | 6/1994 | Long et al. ................. 606/28 |
| 5,649,924 A | | 7/1997 | Everett et al. ............... 606/15 |
| 5,951,543 A | * | 9/1999 | Bruaer ....................... 606/10 |
| 6,294,757 B1 | * | 9/2001 | Whittenbury .......... 219/121.72 |
| 6,476,347 B1 | * | 11/2002 | Whittenbury .......... 219/121.67 |

FOREIGN PATENT DOCUMENTS

| | | |
|---|---|---|
| EP | 0 372 362 A | 6/1990 |
| WO | WO 99/00062 | 1/1999 |

* cited by examiner

Primary Examiner—Roy D. Gibson
Assistant Examiner—Aaron Roane
(74) Attorney, Agent, or Firm—Jenkens & Gilchrist, P.C.

(57) ABSTRACT

A cutting blade for a surgical instrument comprising a body formed of diamond, a cutting edge (16), and refracting means (12) through which laser radiation entering the body of the cutting blade is refracted away from a focal point. The cutting blade also includes a reflective surface (14) having a generally parabolic shape formed within the body of the cutting blade which is positioned to reflect laser radiation entering the cutting blade through the refracting means towards the curing edge of the blade.

12 Claims, 3 Drawing Sheets

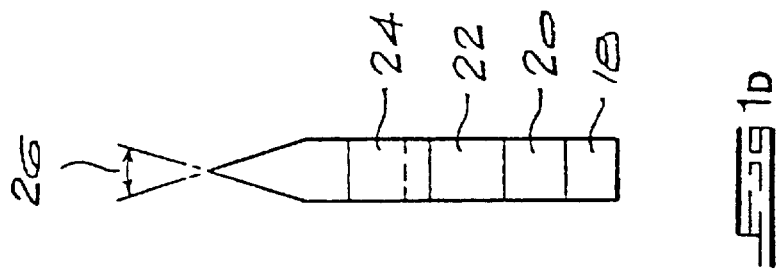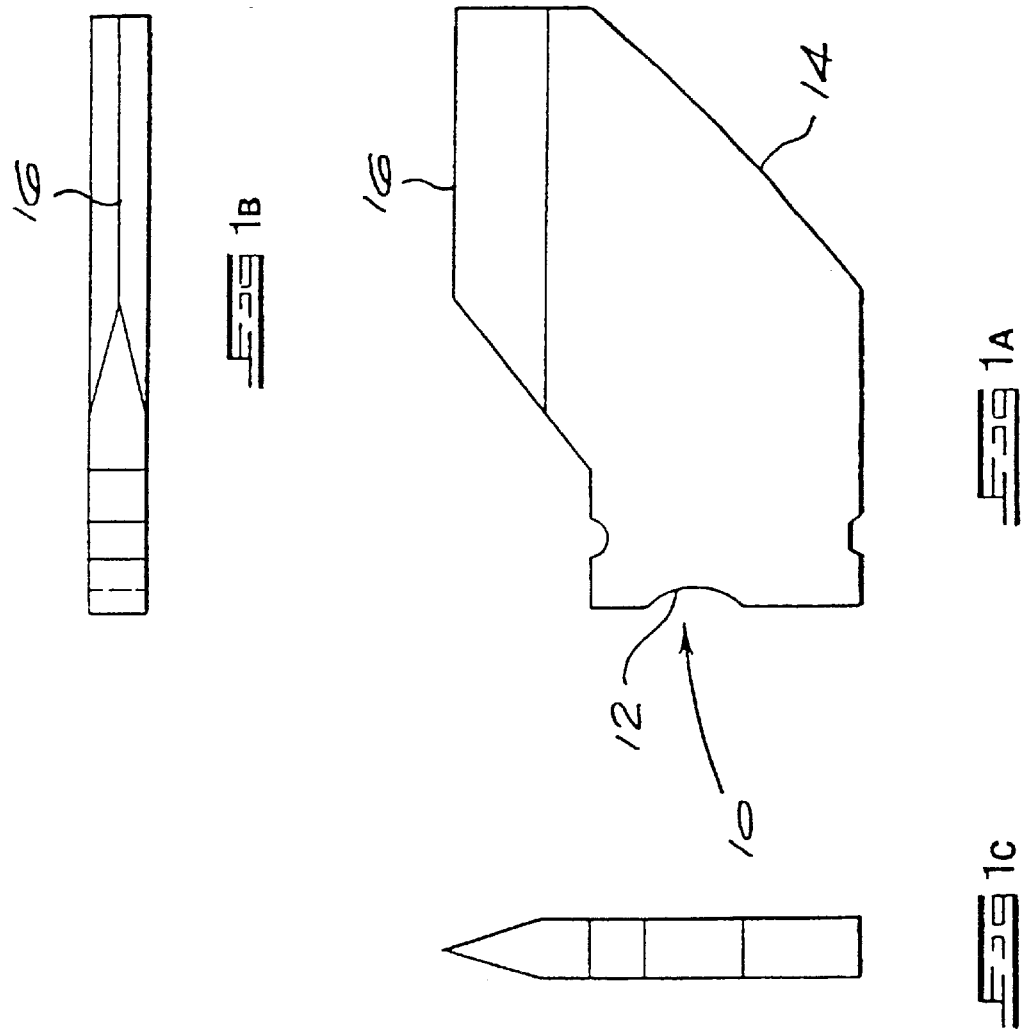

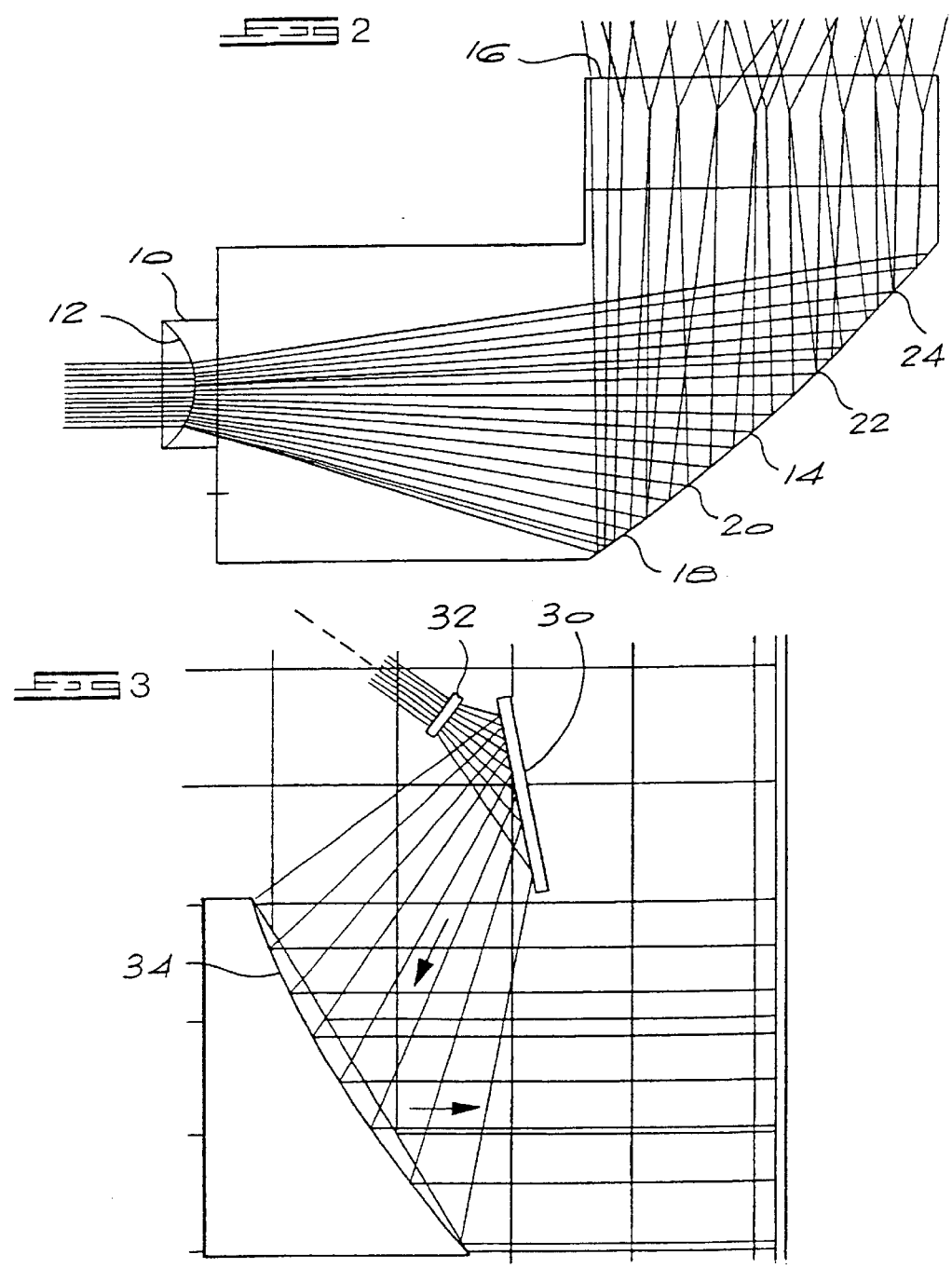

CUTTING BLADE FOR SURGICAL INSTRUMENT

BACKGROUND TO THE INVENTION

This invention relates to a cutting blade for a surgical instrument.

The use of lasers is well established in opthalmology, otolaryngology, gynaecology, dermatology and plastic surgery. The types of lasers that are used are numerous and varied with the type of laser that is used for a particular surgical procedure depending upon the desired laser—tissue interaction.

Visible, ultraviolet and near infra-red laser light have been combined with surgical blades to provide precise control of the application of laser radiation and/or to provide a means of coagulating blood adjacent an incision. U.S. Pat. No. 4,126,136 of Auth et al. describes a transparent scalpel blade connected to a fibre optic waveguide which transports laser radiation to the blade. The blade, which is preferably formed of synthetic sapphire, emits laser radiation through the tapered cutting edge to photocoagulate the blood. U.S. Pat. No. 4,627,435 of Hoskins discloses a surgical knife formed of a diamond blade optically coupled to a Nd:YAG (neodymium:yttrium-aluminium-garnet) laser by a fibre optic bundle. The diamond blade is heated by the laser radiation to provide a cauterizing action while making the incision. The diamond blade may also be coupled to a visible laser to provide illumination for enhanced visibility of the incision site.

U.S. Pat. No. 4,693,244 of Daikuzono describes an artificial sapphire blade coupled to a quartz optical fibre to transmit radiation from a Nd:YAG laser. The sapphire blade is heated by the radiation to coagulate the blood at an incision made with a separate surgical blade. U.S. Pat. No. 5,320,620 of Long et al, describes a laser surgical device with a blunt light emitting element for coagulation. The blade, which may be formed of sapphire, silica or YAG, is coupled to an optical fibre for receiving laser energy. The blade may be coated with a high melting point material to absorb the radiation and heat the blade. U.S. Pat. No. 5,194,712 of Jones describes a single crystal diamond cutting tool with an anti-reflection coating bonded to the entry and exit faces of the cutting tool to provide efficient transfer of laser light, or to communicate laser light at the desired incision.

Of the different types of infra-red laser, which include $CO_2$ and Nd:YAG, $CO_2$ lasers are most widely used for surgical applications of ablation and cutting of tissue. Owing to its position in the far infra-red region of the electromagnetic spectrum, the $CO_2$ laser cannot be delivered through quartz, fibre optics or silica or sapphire lenses, since these materials are opaque to 10 micron wavelength light and absorb infra-red laser radiation. Materials that are commonly used with $CO_2$ laser light, both as lenses and as mirrors, including sodium chloride, potassium chloride, zinc selenide and germanium. $CO_2$ laser light is typically directed through a series of mirrors in a complex articulating system- through which the light is delivered to a handpiece containing a lens which will allow the beam to be focused in a non-contact manner into the target location.

SUMMARY OF THE INVENTION

According to the invention there is provided a cutting blade for a surgical instrument comprising:

a body formed of diamond;

a cutting edge; and refracting means provided at a position remote from the cutting edge through which laser radiation entering the body of the cutting blade is refracted away from a focal point.

The cutting blade may include a reflective surface formed within the body of the cutting blade which is positioned to reflect laser radiation entering the cutting blade through the refracting means towards the cutting edge of the blade.

Preferably, the reflective surface reflects the laser radiation by means of total internal reflection.

Typically, the reflective surface has a generally parabolic shape in cross-section.

Ideally, the parabolic shape of the reflective surface has a focal line generally in common with the focal line of the refracting means.

The generally parabolic shape of the reflective surface may be formed by a series of planar sections arranged adjacent to one another in a curved arrangement.

The laser radiation is typically infra-red laser radiation, more specifically the radiation emitting from a $CO_2$ laser.

Conveniently, the refracting means is an optical lens.

In a preferred embodiment of the invention the optical lens may comprise a cylindrical concave surface formed in a face of the body of the blade.

The cutting edge of the cutting blade may be formed along the edge between two faces having an included angle between them of approximately 60 degrees or less, preferably 36 degrees.

According to the invention there is also provided a surgical blade incorporating a cutting blade as is described above.

Various embodiments of the invention are described in detail in the following passages of the specification which refer to the accompanying drawings. The drawings, however, are merely illustrative of how the invention might be put into effect, so that the specific form and arrangement of the features shown is not to be understood as limiting on the invention.

BRIEF DESCRIPTION OF THE ACCOMPANYING DRAWINGS

FIG. 1a is a side view of a first embodiment of a surgical blade according to the invention;

FIG. 1b is a top view of the surgical blade depicted in FIG. 1a;

FIG. 1c is a left end view of the surgical blade depicted in FIG. 1a;

FIG. 1d is a right end view of the surgical blade depicted in FIG. 1b;

FIG. 2 is a diagrammatic representation of the passage of light through the surgical blade depicted in FIGS. 1a to 1d;

FIG. 3 is a diagrammatic representation of the passage of light through a second embodiment of the invention.

DESCRIPTION OF VARIOUS EMBODIMENTS

Figure 4:
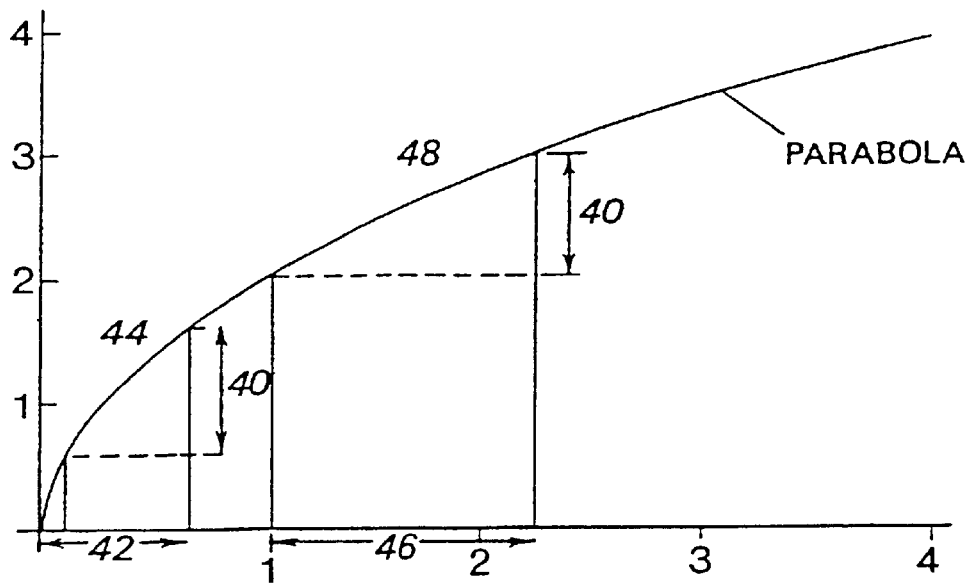
FIG. 4 is a graphical representation of one of the benefits of the second embodiment of the invention. This benefit is described in more detail below.

As is described above in the Background to the Invention, the use of $CO_2$ lasers is well known in surgical applications in particular those involving cauterization, owing to their advantages of less tissue damage and blood loss as compared with other types of lasers.

It is an object of this invention to provide a cutting blade for a surgical instrument. The cutting blade is formed of diamond which is optically designed so as to achieve an even distribution of laser radiation along the cutting edge of the blade such that the cauterization effect is achieved over the entire length of the edge. Specifically, it is important to maximise the cauterization effect at the tip of the cutting blade where the deepest incision is made.

Diamond is transparent, non-hygroscopic and non-toxic and is suitable as a material for a cutting blade owing to its hardness and the sharpness that can be achieved on a sharpened edge.

Two embodiments of the invention are depicted in the accompanying drawings.

In the first embodiment of the invention (depicted in FIG. 1) the laser beam enters the surgical blade off-centre through a concave cylindrical lens 10 having a polished back face 12.

The lens refracts the laser radiation as if it were emerging from the focal line of the cylindrical lens. The body of the surgical blade is formed of diamond which allows the laser radiation to pass freely through it.

Referring to FIG. 1, in cross-section the surgical blade has a parabolic face 14 opposite the cutting edge 16 of the blade. The focal line of the parabolic surface coincides with the focal line of the cylindrical lens. The configuration of the parabolic surface and the cylindrical lens within the body of the surgical blade are such that laser radiation entering the body through the cylindrical lens hits the parabolic surface at an angle of more than 24 degrees with the normal. This angle is critical as in the desired range total internal reflection of the radiation occurs and no radiation leaves the surgical blade on the parabolic surface. With the focal point of the parabolic surface coinciding with the focal point of the cylindrical lens laser radiation entering the body of the surgical blade through the cylindrical lens is reflected by the parabolic surface and is directed towards the cutting edge of the surgical blade as is diagrammatically depicted in FIG. 2.

Arising out of the difficulties in manufacturing a surface having a parabolic shape, the shape of the parabolic surface is approximated with a number of planar sections or facets. With reference to FIG. 2, it can be seen that in this embodiment of the invention four straight facets 18, 20, 22, 24 have been used to approximate the parabolic shape. It will be appreciated that this approximation of the parabolic surface gives rise to a degree of non-uniformity in the radiation density approaching the cutting edge from the surgical blade. It has been found that when at least three or more facets are used to approximate the parabolic surface the variation in radiation density is within acceptable limits.

A further characteristic of the embodiment of the invention depicted in FIG. 1 is that the included angle 26 of the cutting edge of the blade is 60 degrees or less 25 to 36 degrees is the preferred angle for the cutting edge of the blade. If this angle is between 39 and 57 degrees the reflected laser radiation will be reflected internally by the faces or facets of the cutting edge such that little, if any, radiation is emitted through the facets since most of it is reflected back into the body of the surgical blade by total internal reflection.

In the second embodiment of the invention depicted in FIG. 3 of the accompanying drawings, a mirrored surface 30 is interposed in the path of light between the cylindrical lens 32 and the parabolic surface 34 of the surgical blade. The effect of this mirrored or reflective surface is to allow the laser radiation source to be orientated at an angle relative to the cutting edge of the surgical blade. In the first embodiment of the invention depicted in FIGS. 1 and 2 the laser radiation source was arranged in a generally orthogonal relationship to the cutting edge of the blade. This second embodiment of the invention has two advantages over the first embodiment described above. These are:

1. The cutting edge of the surgical blade is arranged at an angle to the body of the cutting instrument on which the surgical blade is mounted. This has ergonomic benefits as it allows a surgeon to cut, for example inside body cavities, without the blade handle interfering with the sides of the incision and/or the tissue.
2. It allows the use of a narrower diamond which reduces the manufacturing cost of the surgical blade. This effect is best described with reference to FIG. 4. For the same width cutting edge 40 a narrower blade 42 can be used if the light is reflected off a steeper part of the parabola 44 than the width of the blade 46 if the light if reflected off a flatter part 48 of the parabola. Either the parabola can be made steeper to achieve this effect or the angle of incidence of the light relative to the surface can be adjusted. This second option is achieved if a mirrored surface is used as can be seen in FIG. 3.

What is claimed is:

1. A cutting blade for a surgical instrument comprising:
   a body formed of diamond;
   a cutting edge; and
   optical lens defining a focal point or focal line provided at a position remote from the cutting edge through which laser radiation entering the body of the cutting blade is divergently refracted through the body with respect to the focal point or focal line.

2. The cutting blade according to claim 1, wherein there is provided a reflective surface formed within the body of the cutting blade which is positioned to reflect laser radiation entering the cutting blade through the refracting means towards the cutting edge of the blade.

3. The cutting blade according to claim 2, wherein the reflective surface reflects the laser radiation by means of total internal reflection.

4. The cutting blade according to claim 2, wherein the reflective surface defines a generally parabolic edge.

5. The cutting blade according to claim 4, wherein the parabolic edge of the reflective surface has a focal line coinciding with the focal line of the refracting means.

6. The cutting blade according to claim 4, wherein the generally parabolic edge of the reflective surface is formed by a series of planar sections arranged adjacent to one another in a curved arrangement.

7. The cutting blade according to claim 1, wherein the laser radiation is infra-red laser radiation.

8. The cutting blade according to claim 7, wherein the infra-red laser radiation is the radiation emitting from a $CO_2$ laser.

9. The cutting blade according to claim 1, wherein the optical lens comprises a cylindrical concave surface formed in a face of the body of the blade.

10. The cutting blade according to claim 1, wherein the cutting edge of the cutting blade is formed along the edge between two faces having an included angle between them of 60 degrees or less.

11. The cutting blade according to claim 10, wherein the cutting edge of the cutting blade is formed along the edge between two faces having an included angle between the range of 25 to 36 degrees.

12. A surgical blade incorporating a cutting blade, said surgical blade comprising:
   a body formed of diamond;
   a cutting edge; and
   optical lens defining a focal point or focal line provided at a position remote from the cutting edge through which laser radiation entering the body of the cutting blade is divergently refracted through the body with respect to the focal point or focal line.

* * * * *